(12) United States Patent
Dixit et al.

(10) Patent No.: US 8,101,597 B2
(45) Date of Patent: Jan. 24, 2012

(54) QUETIAPINE SALTS AND THEIR POLYMORPHS

(75) Inventors: Girish Dixit, Bangalore (IN); Anil Shahaji Khile, Bangalore (IN); Jayesh Laljibhai Patel, Bangalore (IN); Nitin Sharadchandra Pradhan, Maharashtra (IN); Jon Valgeirsson, Hafnarfjordur (IS)

(73) Assignee: Actavis Group PTC EHF (IS)

( * ) Notice: Subject to any disclaimer, the term of this patent is extended or adjusted under 35 U.S.C. 154(b) by 0 days.

(21) Appl. No.: 12/599,085

(22) PCT Filed: May 7, 2008

(86) PCT No.: PCT/IB2008/002341
§ 371 (c)(1),
(2), (4) Date: May 14, 2010

(87) PCT Pub. No.: WO2009/004480
PCT Pub. Date: Jan. 8, 2009

(65) Prior Publication Data
US 2010/0278878 A1 Nov. 4, 2010

(30) Foreign Application Priority Data
May 7, 2007 (IN) .............................. 962/CHE/2007

(51) Int. Cl.
*A61P 25/18* (2006.01)
*A61K 31/55* (2006.01)
*C07D 281/16* (2006.01)
(52) U.S. Cl. .................. 514/211.13; 540/551
(58) Field of Classification Search ............. 514/211.13; 540/551
See application file for complete search history.

(56) References Cited

U.S. PATENT DOCUMENTS

| 4,879,288 A | 11/1989 | Warawa et al. |
| 6,372,734 B1 | 4/2002 | Snape |
| 2006/0063927 A1 | 3/2006 | Etlin et al. |
| 2007/0072840 A1 | 3/2007 | Pandya et al. |

FOREIGN PATENT DOCUMENTS

| EP | 0240228 A1 | 10/1987 |
| WO | 03080065 A1 | 10/2003 |
| WO | 2004078735 A1 | 9/2004 |
| WO | 2005012274 A1 | 2/2005 |
| WO | 2005028457 A1 | 3/2005 |
| WO | 2005028458 A1 | 3/2005 |
| WO | 2005028459 A1 | 3/2005 |
| WO | 2006056772 A2 | 6/2006 |
| WO | 2007048870 A1 | 5/2007 |
| WO | 2007102074 A2 | 9/2007 |
| WO | 2008003270 A1 | 1/2008 |

OTHER PUBLICATIONS

International Search Report and Written Opinion; International Application No. PCT/IB2008/002341; International Filing Date May 7, 2008; Applicant's File Reference APW0080160; Date of Mailing Sep. 16, 2009; 14 pages.

*Primary Examiner* — Brenda Coleman
(74) *Attorney, Agent, or Firm* — Cantor Colburn LLP

(57) ABSTRACT

The present invention relates to novel and stable salt forms of quetiapine, processes for preparation, pharmaceutical compositions, and method of treating thereof. More particularly, the present invention provides novel acid addition salts of quetiapine wherein the acid counter ion is provided by an acid selected from the group consisting of benzene sulfonic acid, dibenzoyl-L-(+)-tartaric acid and di-p-toluoyl-L-(+)-tartaric acid. The present invention also provides novel polymorphic forms of quetiapine salts selected from the group consisting of quetiapine hydrobromide, quetiapine sulfate, quetiapine nitrate and quetiapine citrate.

8 Claims, 7 Drawing Sheets

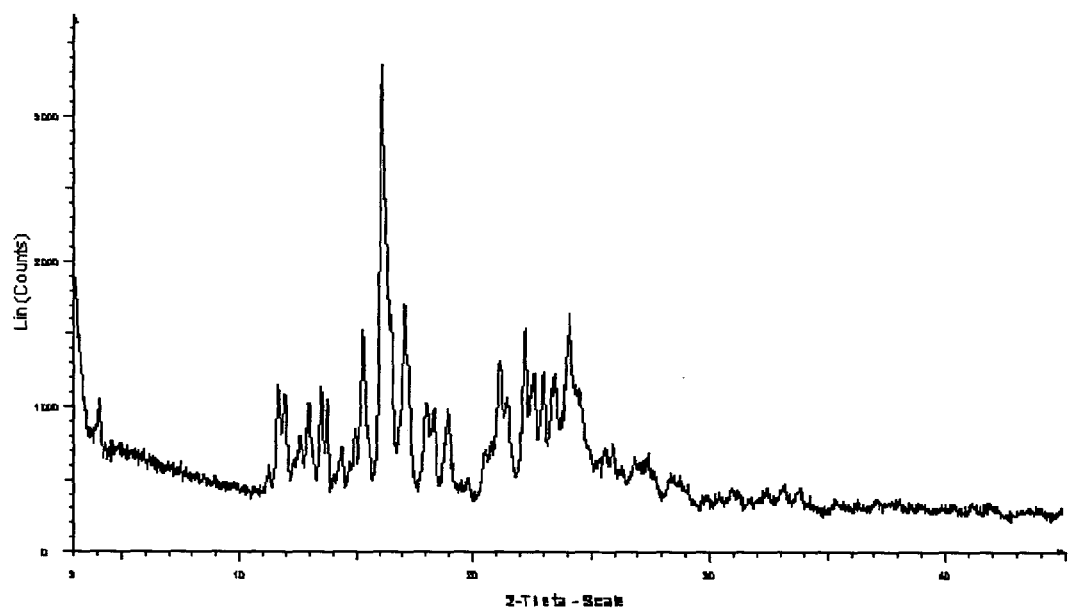
Figure 1: Powder X-ray diffraction (XRD) pattern of crystalline quetiapine besylate salt

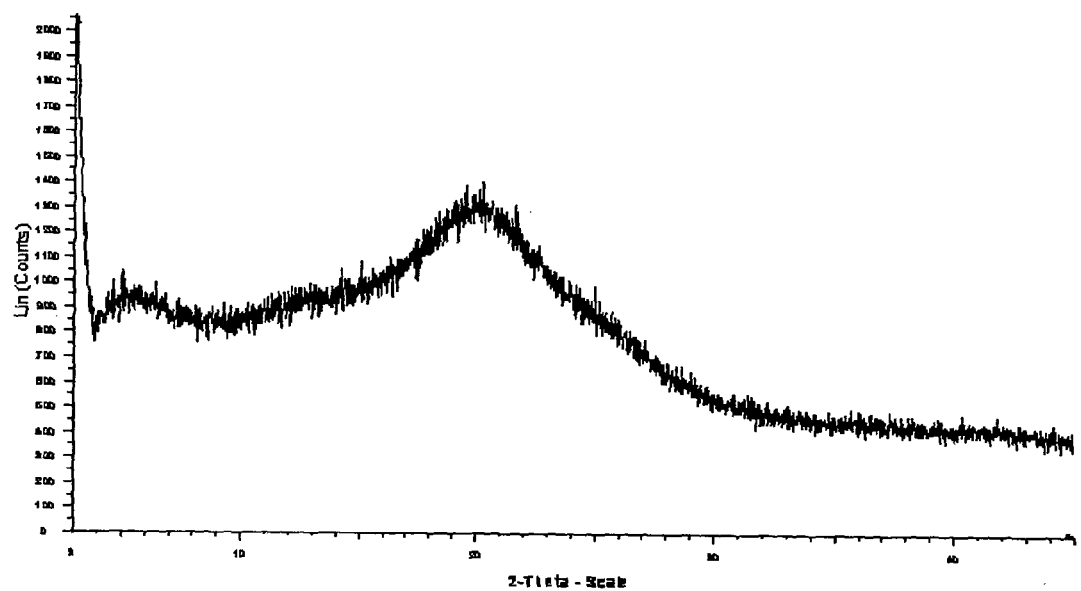
Figure 2: Powder X-ray diffraction (XRD) pattern of amorphous quetiapine dibenzoyl-L-(+)-tartarate salt

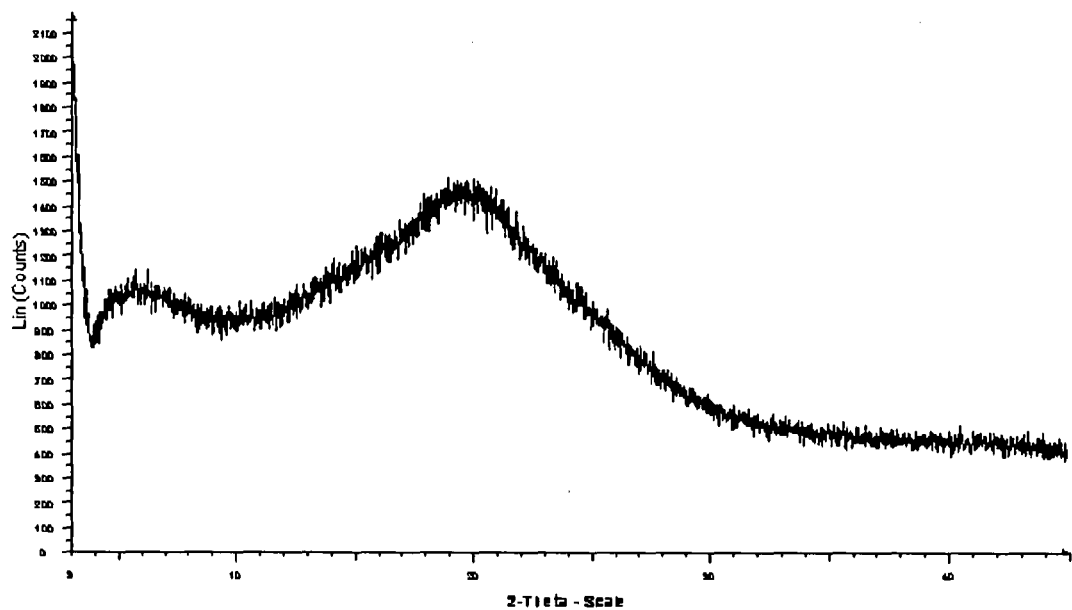
Figure 3: Powder X-ray diffraction (XRD) pattern of amorphous quetiapine di-p-toluoyl-L-(+)-tartarate salt

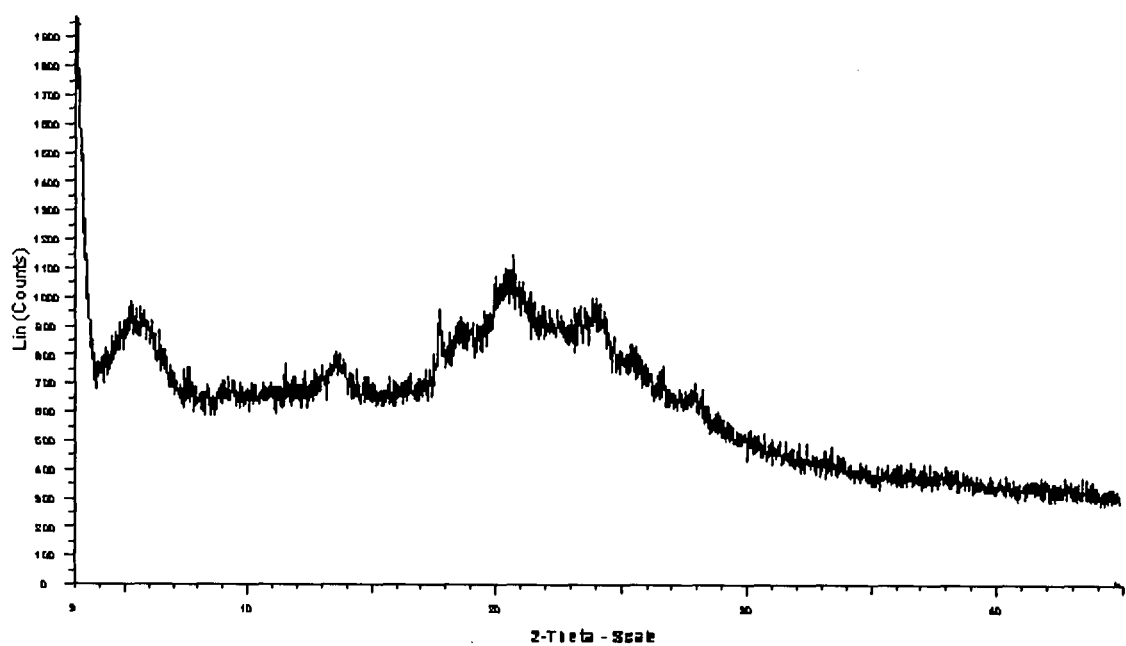
Figure 4: Powder X-ray diffraction (XRD) pattern of amorphous quetiapine nitrate

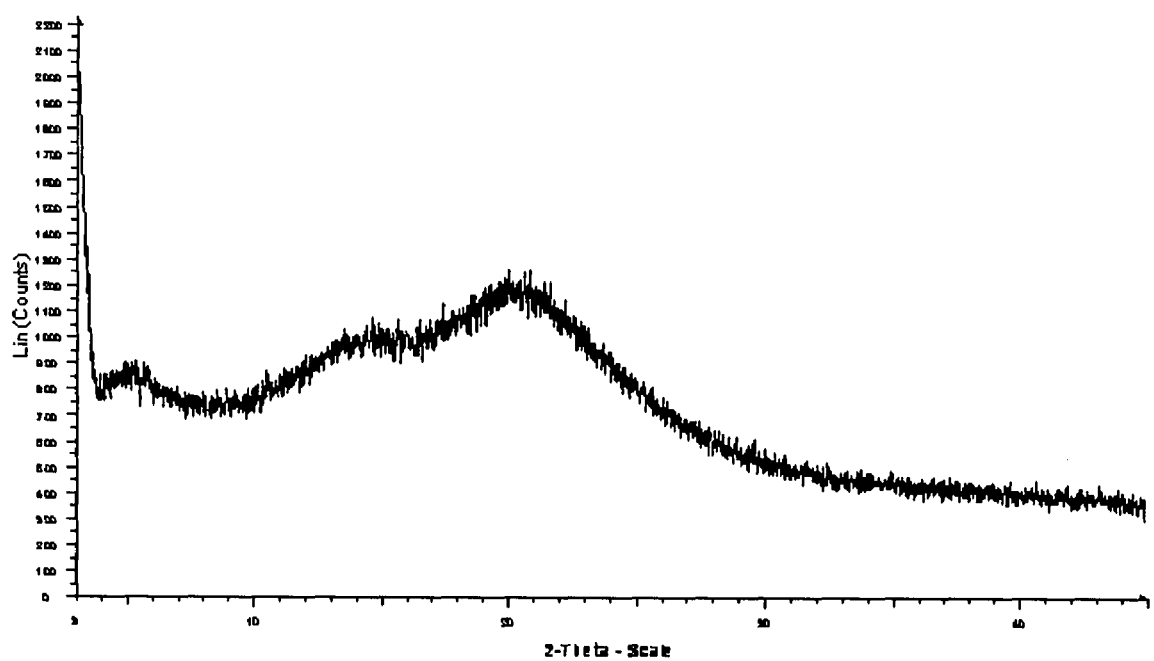
Figure 5: Powder X-ray diffraction (XRD) pattern of amorphous quetiapine citrate

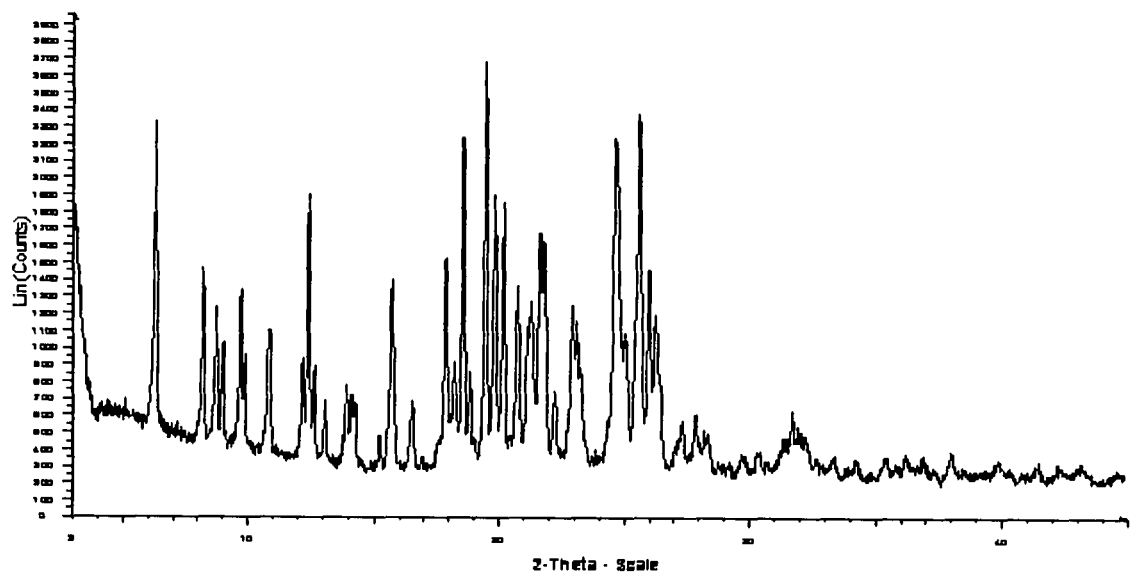
Figure 6: Powder X-ray diffraction (XRD) pattern of crystalline Form A of quetiapine sulfate

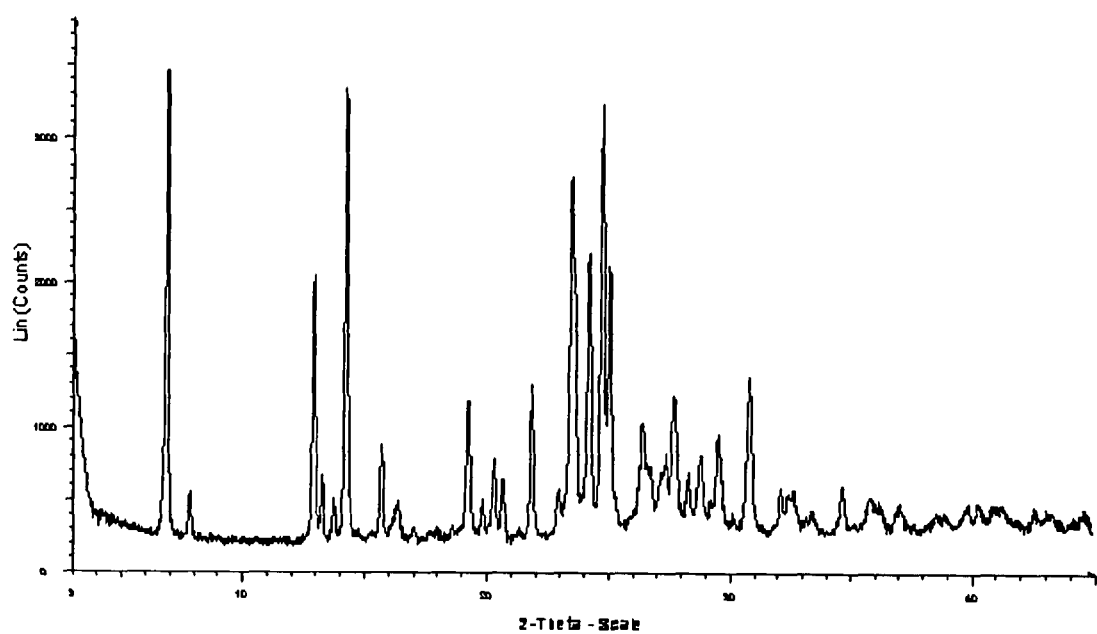
Figure 7: Powder X-ray diffraction (XRD) pattern of crystalline Form B of quetiapine hydrobromide

QUETIAPINE SALTS AND THEIR POLYMORPHS

CROSS-REFERENCE TO RELATED APPLICATIONS

This application is a 371 of PCT/IB2008/002341 filed May 7, 2008, which claims the benefit of the filing date of May 7, 2007 to Indian Application No. 962/CHE/2007 under provisions of 35 U.S.C. §119 and the International Convention for the protection of Industrial Property.

FIELD OF THE DISCLOSURE

The present invention relates to novel and stable salt forms of quetiapine, processes for preparation, pharmaceutical compositions, and method of treating thereof. More particularly, the present invention provides novel acid addition salts of quetiapine wherein the acid counter ion is provided by an acid selected from the group consisting of benzene sulfonic acid, dibenzoyl-L-(+)-tartaric acid and di-p-toluoyl-L-(+)-tartaric acid. The present invention also provides novel polymorphic forms of quetiapine salts selected from the group consisting of quetiapine hydrobromide, quetiapine sulfate, quetiapine nitrate and quetiapine citrate.

BACKGROUND OF THE INVENTION

Quetiapine, also known as 11-[4-[2-(2-Hydroxyethoxy) ethyl]-1-piperazinyl]-dibenzo[b,f][1,4]thiazepine and represented by the following structural formula:

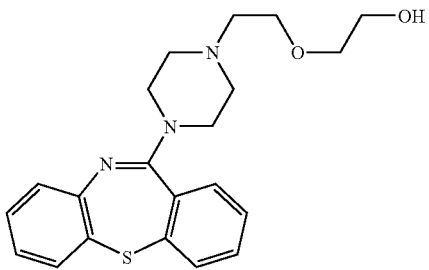

Quetiapine is a psychoactive organic compound that acts as an antagonist for multiple neurotransmitter receptors in the brain and acts as an antipsychotic agent reportedly useful for treating, among other things, schizophrenia. This drug was approved under the trademark Seroquel®, by the U.S. Food and Drug Administration and it is available in the form of its hemifumarate salt. Quetiapine hemifumarate is a psychotropic agent belonging to the chemical class of dibenzothiazepine derivatives and its first synthesis was disclosed in U.S. Pat. No. 4,879,288.

U.S. Pat. No. 4,879,288 (herein after referred to as the '288 patent) discloses a process for the preparation of quetiapine or pharmaceutically acceptable salts thereof which includes hydrochloride, maleate, fumarate, citrate, phosphonate, methane sulphonate, and hemifumarate salt.

While the '288 patent mentions that the compound of formula II (quetiapine) can form a salt with physiologically acceptable organic and inorganic acids like hydrochloride, maleate, fumarate, citrate, phosphonate, methane sulphonate, and hemifumarate salt, only the hydrochloride, maleate and hemifumarate salts of quetiapine have been prepared.

Various processes have been reported for the preparation of quetiapine or pharmaceutically acceptable salts thereof in European patent EP 282236; PCT Publication Nos. WO 05/012274; 05/028457; 05/028458; and 05/028459.

U.S. Pat. No. 6,372,734 provides a process for the purification of crystalline quetiapine or pharmaceutically acceptable salts thereof which includes hydrochloride, maleate, fumarate, citrate, phosphonate, methane sulphonate, in particular the hemifumarate salt, which involves crystallizing quetiapine freebase.

U.S. Patent Application No. 2006/0063927 A1 (herein after referred to as the '927 application) teaches a general preparation of pharmaceutically acceptable salts of quetiapine which comprises treating quetiapine free base with at least a stoichiometric amount of an appropriate acid, wherein the appropriate acid includes, but are not limited to, inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. While the '927 application mentions a general preparation of several acid addition salts of quetiapine; only the hemifumarate salt of quetiapine has been prepared.

PCT Publication No. WO 2006/056772 A2 discloses organic acid addition salts of quetiapine selected from the group consisting of oxalate, succinate, benzoate and formate, specifically in crystalline forms along with their XRD patterns and melting points.

U.S. Patent Application No. 2007/0072840 A1 discloses polymorphic forms of quetiapine hydrochloride designated as Forms A, B, C & amorphous, and processes for their preparation. The '840 application further discloses oxalate and maleate salts of quetiapine, specifically in crystalline forms, and processes for their preparation.

PCT Publication No. WO 2007/048870 A1 teaches a process for preparing and purifying crystalline quetiapine hemifumarate which comprises dissolving quetiapine base in a solvent, converting quetiapine base to the first quetiapine salt, cooling the mixture to precipitate the first quetiapine salt, isolating the first quetiapine salt, and converting the first quetiapine salt to quetiapine hemifumarate salt; wherein the salts which is used as first crystallization salts are e.g. tosylate or hydrohalic acid salts, preferably hydrochloride.

PCT Publication No. WO 2007/102074 A2 discloses acid addition salts of quetiapine selected from the group consisting of malate (designated as Form I characterized by a powder X-ray diffraction pattern having peaks expressed as 2-theta at about 7.1, 9.0, 16.0, 21.0 degrees), succinate (designated as Form II characterized by a powder X-ray diffraction pattern having peaks expressed as 2-theta at about 7.4, 9.3, 20.0, 22.5 degrees), tosylate (designated as Form III characterized by a powder X-ray diffraction pattern having peaks expressed as 2-theta at about 11.3, 12.2, 12.7, 13.3, 17.3 degrees), tartrate (designated as Form IV characterized by a powder X-ray diffraction pattern having peaks expressed as 2-theta at about 6.7, 9.4, 19.6, 20.6, 22.3 degrees), benzoate (designated as Form V characterized by a powder X-ray diffraction pattern having peaks expressed as 2-theta at about 6.2, 14.1, 14.8, 19.9, 21.1, 22.1, 23.0 degrees), oxalate (designated as, Form VI characterized by a powder X-ray diffraction pattern having peaks expressed as 2-theta at about 7.3, 10.7, 11.8, 22.4 degrees; Form VII characterized by a powder X-ray diffraction pattern having peaks expressed as 2-theta at about 9.6, 12.6, 14.5, 16.8, 24.1 degrees), and hydrobromide (designated as Form VIII characterized by a powder X-ray diffraction pattern having peaks expressed as 2-theta at about 5.6, 16.6, 23.8, 24.8 and 26.4).

PCT Publication No. WO 2008/003270A1 discloses a method for the preparation of salts of quetiapine from the quetiapine base and the respective acid, specifically fumaric acid and oxalic acid, characterized in that the reaction is carried out in a mixture of solvents, the mixture being either a mixture of an aromatic hydrocarbon and a ketone or ester, or that of an aromatic hydrocarbon, water and a ketone or ester.

In the formulation of drug compositions, it is important for the active pharmaceutical ingredient to be in a form in which it can be conveniently handled and processed. This is of critical, not only from the point of view of obtaining a commercially viable manufacturing process, but also from the point of view of subsequent manufacture of pharmaceutical formulations (e.g. oral dosage forms such as tablets) comprising the active pharmaceutical ingredient.

Further, in the manufacture of oral pharmaceutical compositions, it is important that a reliable, reproducible and constant plasma concentration profile of the active pharmaceutical ingredient is provided following administration to a patient.

Chemical stability, solid state stability, and "shelf life" of the active pharmaceutical ingredient are important properties for a pharmaceutical active compound. The active pharmaceutical ingredient, and compositions containing it, should be capable of being effectively stored over appreciable periods of time, without exhibiting a significant change in the physico-chemical characteristics of the active pharmaceutical ingredient, e.g. its chemical composition, density, hygroscopicity and solubility. Thus, in the manufacture of commercially viable and pharmaceutically acceptable drug compositions, it is important, wherever possible, to provide the active pharmaceutical ingredient in a stable form.

The discovery of new salts of a pharmaceutically useful compound provides a new opportunity to improve the performance characteristics of a pharmaceutical product. It also adds value to the material that a formulation scientist can use the same for designing, for example, a pharmaceutical dosage form of a drug with a targeted release profile or other desired characteristic. Novel salts of quetiapine have now been discovered.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Solvent medium and mode of crystallization play very important role in obtaining a new salt or a crystalline form over the other.

The discovery of new polymorphic forms of a pharmaceutically useful compound provides a new opportunity to improve the performance characteristics of a pharmaceutical product. It also adds to the material that a formulation scientist has available for designing, for example, a pharmaceutical dosage form of a drug with a targeted release profile or other desired characteristic. Novel and stable polymorphic forms of quetiapine salts have now been discovered.

SUMMARY OF THE INVENTION

According to one aspect of the present invention, there is provided a novel salt form of quetiapine, wherein the salt is a besylate, dibenzoyl-L-(+)-tartrate, di-p-toluoyl-L-(+)-tartrate, nitrate, citrate, sulfate or hydrobromide.

In another aspect, quetiapine salts in a solid state is provided. In another aspect, quetiapine salts in a crystalline form is provided. In yet another aspect, quetiapine salts in an amorphous form is provided. In another aspect, the salts of quetiapine may exist in an anhydrous and/or solvent-free form or as a hydrate and/or a solvate.

It has also been found that the novel salt forms of quetiapine are useful intermediates in the preparation of quetiapine free base or a pharmaceutically acceptable salt thereof in high purity. The salt forms of quetiapine have good flow properties and are far more stable at room temperature, enhanced temperature and at relative high humidities and in aqueous media, and so, the novel salt forms are suitable for formulating quetiapine.

In another aspect, the present invention encompasses a process for preparing the novel salt forms of quetiapine which comprises contacting quetiapine free base with a suitable acid in a suitable solvent under suitable conditions, and isolating the appropriate salt forms of quetiapine, wherein the suitable acid is selected from the group consisting of benzenesulfonic acid, dibenzoyl-L-(+)-tartaric acid, di-p-toluoyl-L-(+)-tartaric acid, nitric acid, citric acid, sulfuric acid and hydrobromic acid.

The suitable solvent is selected from the group comprising water, alcohols, ketones, ethers, hydrocarbons, chlorinated hydrocarbons, nitriles, esters and the like, and mixtures thereof. Most preferable solvents are ketones, ethers, alcohols, and mixtures thereof.

Exemplary alcohol solvents include, but are not limited to, $C_1$ to $C_8$ straight or branched chain alcohol solvents such as methanol, ethanol, propanol, butanol, amyl alcohol, hexanol, and mixtures thereof. Specific alcohol solvents are methanol, ethanol, isopropyl alcohol, and mixtures thereof, and most specific alcohol solvent is isopropyl alcohol. Exemplary ketone solvents include, but are not limited to, acetone, methyl ethyl ketone, methyl isobutyl ketone, methyl tert-butyl ketone and the like, and mixtures thereof. Exemplary ether solvents include, but are not limited to, diisopropyl ether, diethyl ether, tetrahydrofuran, dioxane, and the like, and mixtures thereof. Exemplary nitrile solvents include, but are not limited to, acetonitrile and the like, and mixtures thereof. Exemplary ester solvents include, but are not limited to, ethyl acetate, isopropyl acetate, and the like and mixtures thereof. Exemplary hydrocarbon solvents include, but are not limited to, n-pentane, n-hexane and n-heptane and their isomers, cyclohexane, toluene, xylene, and mixtures thereof. Exemplary chlorinated hydrocarbon solvents include, but are not limited to, methylene chloride, ethyl dichloride, chloroform and carbon tetrachloride or mixtures thereof. Specific chlorinated hydrocarbon solvent is methylene chloride.

In another aspect, the present invention provides methods for treating or preventing psychosis associated with schizophrenia, comprising administering the salt forms of quetiapine, or a pharmaceutical composition that comprises salt forms of quetiapine, along with pharmaceutically acceptable excipients.

In another aspect, the present invention provides pharmaceutical compositions comprising a therapeutically effective amount of the quetiapine salt forms of the present invention, and one or more pharmaceutically acceptable excipients.

In another aspect, the present invention provides pharmaceutical compositions comprising the salt forms of quetiapine prepared according to processes of the present invention in any of its embodiments and one or more pharmaceutically acceptable excipients.

In yet another aspect, the present invention further encompasses a process for preparing a pharmaceutical formulation comprising combining any one of the salt forms of quetiapine prepared according to processes of the present invention in any of its embodiments, with one or more pharmaceutically acceptable excipients.

In another aspect, the substantially pure salt forms of quetiapine disclosed herein for use in the pharmaceutical compositions of the present invention, wherein 90 volume-percent of the particles ($D_{90}$) have a size of less than or equal to about 500 microns, specifically less than or equal to about 300 microns, more specifically less than or equal to about 200 microns, still more specifically less than or equal to about 100 microns, and most specifically less than or equal to about 15 microns.

In another aspect, the present invention provides substantially pure salt forms of quetiapine having relatively low content of one or more organic volatile impurities.

Unless otherwise indicated, the following definitions are set forth to illustrate and define the meaning and scope of the various terms used to describe the invention herein.

The term "solid form of novel salts of quetiapine disclosed herein" includes crystalline forms, amorphous form, hydrated and solvated forms of quetiapine salts.

The term "crystalline polymorph" refers to a crystal modification that can be characterized by analytical methods such as X-ray powder diffraction, IR-spectroscopy, differential scanning calorimetry (DSC) or by its melting point.

The term "amorphous" means a solid without long-range crystalline order. Amorphous form of quetiapine salts; particularly, quetiapine nitrate, quetiapine citrate, quetiapine dibenzoyl-L-(+)-tartrate, quetiapine di-p-toluoyl-L-(+)-tartarate; in accordance with the present invention preferably contains less than about 10% crystalline forms of quetiapine salt, more preferably less than 5% crystalline form of quetiapine salt, and still more preferably is essentially free of crystalline forms of quetiapine salt. "Essentially free of crystalline forms of quetiapine salt" means that no crystalline polymorph forms of quetiapine salt can be detected within the limits of a powder X-ray diffractometer.

The term "pharmaceutically acceptable" means that which is useful in preparing a pharmaceutical composition that is generally non-toxic and is not biologically undesirable and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions of the present invention encompass any composition made by admixing the active ingredient, active ingredient dispersion or composite, additional active ingredient(s), and pharmaceutically acceptable excipients.

The expression "pharmaceutically acceptable salt" is meant those salts which are, within the scope of sound medical judgment, suitable for use in contact with the tissues of humans and lower animals without undue toxicity, irritation, allergic response and the like, commensurate with a reasonable benefit/risk ratio, and effective for their intended use. Representative alkali or alkaline earth metal salts include the sodium, calcium, potassium and magnesium salts, and the like.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "delivering" as used herein means providing a therapeutically effective amount of an active ingredient to a particular location within a host causing a therapeutically effective blood concentration of the active ingredient at the particular location. This can be accomplished, e.g., by topical, local or by systemic administration of the active ingredient to the host.

The term "buffering agent" as used herein is intended to mean a compound used to resist a change in pH upon dilution or addition of acid of alkali. Such compounds include, by way of example and without limitation, potassium metaphosphate, potassium phosphate, monobasic sodium acetate and sodium citrate anhydrous and dehydrate and other such material known to those of ordinary skill in the art.

The term "sweetening agent" as used herein is intended to mean a compound used to impart sweetness to a formulation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein is intended to mean substances used to cause adhesion of powder particles in granulations. Such compounds include, by way of example and without limitation, acacia alginic acid, tragacanth, carboxymethylcellulose sodium, polyvinylpyrrolidone, compressible sugar (e.g., NuTab), ethylcellulose, gelatin, liquid glucose, methylcellulose, povidone and pregelatinized starch, combinations thereof and other material known to those of ordinary skill in the art. If required, other binders may also be included in the present invention.

Exemplary binders include starch, polyethylene glycol, guar gum, polysaccharide, bentonites, sugars, invert sugars, poloxamers (PLURONIC™ F68, PLURONIC™ F127), collagen, albumin, celluloses in nonaqueous solvents, combinations thereof and the like. Other binders include, for example, polypropylene glycol, polyoxyethylene-polypropylene copolymer, polyethylene ester, polyethylene sorbitan ester, polyethylene oxide, microcrystalline cellulose, polyvinylpyrrolidone, combinations thereof and other such materials known to those of ordinary skill in the art.

The term "diluent" or "filler" as used herein is intended to mean inert substances used as fillers to create the desired bulk, flow properties, and compression characteristics in the preparation of solid dosage formulations. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein is intended to mean agents used in solid dosage formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

The term "lubricant" as used herein is intended to mean substances used in solid dosage formulations to reduce friction during compression of the solid dosage. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein is intended to mean a compound used in solid dosage formulations to promote the disruption of the solid mass into smaller particles which are more readily dispersed or dissolved. Exemplary disintegrants include, by way of example and without limitation, starches such as corn starch, potato starch, pregelatinized, sweeteners, clays, such as bentonite, macrocrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

The term "wetting agent" as used herein is intended to mean a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN™s), polyethylene glycols, polyoxyethylene stearates colloidal silicon dioxide, phosphates, sodium dodecylsulfate, carboxymethylcellulose calcium, carboxymethylcellulose sodium, methylcellulose, hydroxyethylcellulose, hydroxyl propylcellulose, hydroxypropylmethylcellulose phthalate, noncrystalline cellulose, magnesium aluminum silicate, triethanolamine, polyvinyl alcohol, and polyvinylpyrrolidone (PVP). Tyloxapol (a nonionic liquid polymer of the alkyl aryl polyether alcohol type, also known as superinone or triton) is another useful wetting agent, combinations thereof and other such materials known to those of ordinary skill in the art.

As used herein, $D_X$ means that X percent of the particles have a diameter less than a specified diameter D. Thus, a $D_{90}$ of less than 300 microns means that 90 volume-percent of the micronized particles in a composition have a diameter less than 300 microns.

The term "micronization" used herein means a process or method by which the size of a population of particles is reduced.

As used herein, the term "micron" or "μm" both are same refers to "micrometer" which is $1\times10^{-6}$ meter.

As used herein, "crystalline particles" means any combination of single crystals, aggregates and agglomerates.

As used herein, "Particle Size Distribution (P.S.D)" means the cumulative volume size distribution of equivalent spherical diameters as determined by laser diffraction in Malvern Master Sizer 2000 equipment or its equivalent. "Mean particle size distribution, i.e., $D_{50}$" correspondingly, means the median of said particle size distribution.

By "substantially pure" is meant having purity greater than about 99%, specifically greater than about 99.5%, and more specifically greater than about 99.9% measured by HPLC.

BRIEF DESCRIPTION OF THE DRAWINGS

FIG. 1 is a characteristic powder X-ray diffraction (XRD) pattern of crystalline quetiapine besylate.

FIG. 2 is a characteristic powder X-ray diffraction (XRD) pattern of amorphous quetiapine dibenzoyl-L-(+)-tartrate.

FIG. 3 is a characteristic powder X-ray diffraction (XRD) pattern of amorphous quetiapine di-p-toluoyl-L-(+)-tartrate.

FIG. 4 is a characteristic powder X-ray diffraction (XRD) pattern of amorphous quetiapine nitrate.

FIG. 5 is a characteristic powder X-ray diffraction (XRD) pattern of amorphous quetiapine citrate.

FIG. 6 is a characteristic powder X-ray diffraction (XRD) pattern of crystalline Form A of quetiapine sulfate.

FIG. 7 is a characteristic powder X-ray diffraction (XRD) pattern of crystalline Form B of quetiapine hydrobromide.

The X-Ray powder diffraction was measured by an X-ray powder Diffractometer equipped with CuKα-radiations (40 kV, 40 mA) in wide-angle X-ray Diffractometer of BRUKER axs, D8 ADVANCE. The sample was analyzed using the following instrument parameters: measuring range=3-45° 2-theta; step width=0.01579°; and measuring time per step=0.11 sec.

DETAILED DESCRIPTION OF THE INVENTION

According to one aspect of the present invention, there is provided a novel salt form of quetiapine, wherein the salt is a besylate, dibenzoyl-L-(+)-tartrate, di-p-toluoyl-L-(+)-tartrate, nitrate, citrate, sulfate or hydrobromide.

In another aspect, quetiapine salts in a solid state is provided. In another aspect, quetiapine salts in a crystalline form is provided. In yet another aspect, quetiapine salts in an amorphous form is provided. In another aspect, the salts of quetiapine may exist in an anhydrous and/or solvent-free form or as a hydrate and/or a solvate.

In another embodiment, the novel salt forms of quetiapine are useful intermediates in the preparation of quetiapine free base or a pharmaceutically acceptable salt thereof in high purity. The salt forms of quetiapine have good flow properties and are far more stable at room temperature, enhanced temperature and at relative high humidities and in aqueous media, and so, the novel salt forms are suitable for formulating quetiapine.

According to another aspect of the present invention, a process for the preparation of a salt form of quetiapine, wherein the salt is selected from the group consisting of besylate, dibenzoyl-L-(+)-tartrate, di-p-toluoyl-L-(+)-tartrate, nitrate, citrate, sulfate and hydrobromide; which comprises:

a) contacting quetiapine free base with a suitable acid in a suitable solvent to produce a reaction mass containing quetiapine acid addition salt;

b) optionally, heating the reaction mass obtained in step-(a); and c) substantially removing the solvent from the reaction mass obtained in step-(a) or step-(b) to afford solid form of quetiapine salt; (or)

d) isolating solid form of quetiapine salt by forcible or spontaneous crystallization;

wherein the suitable acid used in step-(a) is selected from the group consisting of benzenesulfonic acid, dibenzoyl-L-(+)-tartaric acid, di-p-toluoyl-L-(+)-tartaric acid, nitric acid, citric acid, sulfuric acid and hydrobromic acid.

The suitable solvent is selected from the group comprising water, alcohols, ketones, ethers, hydrocarbons, chlorinated hydrocarbons, nitriles, esters and the like, and mixtures thereof. Most preferable solvents are ketones, ethers, alcohols, and mixtures thereof.

Exemplary alcohol solvents include, but are not limited to, $C_1$ to $C_8$ straight or branched chain alcohol solvents such as methanol, ethanol, propanol, butanol, amyl alcohol, hexanol, and mixtures thereof. Specific alcohol solvents are methanol, ethanol, isopropyl alcohol, and mixtures thereof, and most specific alcohol solvent is isopropyl alcohol. Exemplary ketone solvents include, but are not limited to, acetone, methyl ethyl ketone, methyl isobutyl ketone, methyl tert-butyl ketone and the like, and mixtures thereof. Exemplary ether solvents include, but are not limited to, diisopropyl ether, diethyl ether, tetrahydrofuran, dioxane, and the like, and mixtures thereof. Exemplary nitrile solvents include, but are not limited to, acetonitrile and the like, and mixtures thereof. Exemplary ester solvents include, but are not limited to, ethyl acetate, isopropyl acetate, and the like and mixtures thereof. Exemplary hydrocarbon solvents include, but are not limited to, n-pentane, n-hexane and n-heptane and their isomers, cyclohexane, toluene, xylene, and mixtures thereof. Exemplary chlorinated hydrocarbon solvents include, but are not limited to, methylene chloride, ethyl dichloride, chloroform and carbon tetrachloride or mixtures thereof. Specific chlorinated hydrocarbon solvent is methylene chloride.

The reaction in step-(a) is carried out at a temperature of about 0° C. to about 100° C., preferably at about 0° C. to about 80° C., more preferably at about 20° C. to about 60° C.

The reaction mass in step-(b) is preferably heated at a temperature of about 40° C. to the reflux temperature of the solvent used for at least 20 minutes, and more preferably at the reflux temperature of the solvent used from about 30 minutes to about 5 hours.

Removal of solvent in step-(c) is accomplished by, for example, substantially complete evaporation of the solvent, concentrating the solution, and filtering the solid under inert atmosphere. Alternatively, the solvent may also be removed by evaporation. Evaporation can be achieved at sub-zero temperatures by the lyophilisation or freeze-drying technique The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD"), or evaporated by spray drying to obtain a dry amorphous powder.

Spontaneous crystallization refers to crystallization without the help of an external aid such as seeding, cooling etc., and forcible crystallization refers to crystallization with the help of an external aid.

Forcible crystallization may be initiated by a method usually known in the art such as cooling, seeding, partial removal of the solvent from the solution, by adding an anti-solvent to the solution or a combination thereof.

The pure solid form of quetiapine salts obtained in step-(d) may be collected by filtration or centrifugation.

According to another aspect of the present invention, there is provided a crystalline quetiapine besylate salt, characterized by at least one of the following:
i) a powder X-ray diffraction pattern substantially in accordance with FIG. 1;
ii) a powder X-ray diffraction pattern having peaks at about 11.6, 11.9, 13.5, 13.7, 15.3, 16.1, 16.5, 17.0, 17.9, 21.1, 22.2, 22.5 and 24.1±0.2 degrees 2-theta substantially as depicted in FIG. 1; and
iii) a powder X-ray diffraction pattern having additional peaks at about 4.0, 12.5, 12.9, 14.9, 18.3, 18.9, 21.4, 22.9, 23.4 and 24.4±0.2 degrees 2-theta substantially as depicted in FIG. 1.

The crystalline quetiapine besylate salt is stable, consistently reproducible and has good flow properties, and which is particularly suitable for bulk preparation and handling, and so, the novel crystalline quetiapine besylate salt is suitable for formulating quetiapine. Moreover, the crystalline quetiapine besylate is useful intermediate in the preparation of quetiapine or a pharmaceutically acceptable salt thereof in high purity.

According to another aspect of the present invention, a process for the preparation of crystalline quetiapine besylate salt is provided, which comprises:
a) providing a solution of quetiapine free base in a suitable solvent or a mixture of suitable solvents;
b) adding benzenesulfonic acid to the solution obtained in step-(a);
c) optionally, heating the reaction mass obtained in step-(b) to form a clear solution; and
d) isolating crystalline quetiapine besylate from the solution.

The process can produce substantially pure crystalline quetiapine besylate which can be isolated from the reaction mixture in conventional manner.

The suitable solvent is selected from the group comprising water, alcohols, ketones, chlorinated hydrocarbons, nitriles, esters and the like, and mixtures thereof. Most preferable solvents are ketones, alcohols, and mixtures thereof.

Exemplary alcohol solvents include, but are not limited to, $C_1$ to $C_8$ straight or branched chain alcohol solvents such as methanol, ethanol, propanol, butanol, amyl alcohol, hexanol, and mixtures thereof. Specific alcohol solvents are methanol, ethanol, isopropyl alcohol, and mixtures thereof, and most specific alcohol solvent is isopropyl alcohol. Exemplary ketone solvents include, but are not limited to, acetone, methyl ethyl ketone, methyl isobutyl ketone, methyl tert-butyl ketone and the like, and mixtures thereof. Exemplary nitrile solvents include, but are not limited to, acetonitrile and the like, and mixtures thereof. Exemplary ester solvents include, but are not limited to, ethyl acetate, isopropyl acetate, and the like and mixtures thereof. Exemplary chlorinated hydrocarbon solvents include, but are not limited to, methylene chloride, ethyl dichloride, chloroform and carbon tetrachloride or mixtures thereof. Specific chlorinated hydrocarbon solvent is methylene chloride.

Step-(a) of providing a solution of quetiapine free base includes dissolving quetiapine free base in the solvent, or obtaining an existing solution from a previous processing step.

Preferably the quetiapine free base is dissolved in the solvent at a temperature of above about 25° C., more preferably at about 25° C. to about 100° C., and still more preferably at about 25° C. to about 80° C.

The addition of benzenesulfonic acid in step-(b) is preferably carried out at a temperature of below about 50° C. for at least 10 minutes, and more preferably at a temperature of about 25° C. to about 50° C. from about 30 minutes to about 2 hours.

Usually, about 0.2 to 2.0 moles, specifically, about 0.2 to 1.2 moles of benzenesulfonic acid is used per 1 mole of quetiapine base.

The reaction mass in step-(c) is preferably heated at a temperature of about 40° C. to about 80° C. for at least 20 minutes, and more preferably at a temperature of about 40° C. to about 75° C. from about 30 minutes to about 4 hours.

The isolation of pure crystalline quetiapine besylate in step-(d) may be carried out by forcible or spontaneous crystallization.

Spontaneous crystallization refers to crystallization without the help of an external aid such as seeding, cooling etc., and forcible crystallization refers to crystallization with the help of an external aid.

Forcible crystallization may be initiated by a method usually known in the art such as cooling, seeding, partial removal of the solvent from the solution, by adding an anti-solvent to the solution, or a combination thereof.

Preferably the crystallization is carried out by adding an anti-solvent selected from the group consisting of ethers, hydrocarbons, and mixtures thereof. Exemplary ether solvents include, but are not limited to, diisopropyl ether, diethyl ether, tetrahydrofuran, dioxane, and the like, and mixtures thereof. Exemplary hydrocarbon solvents include, but are not limited to, n-pentane, n-hexane and n-heptane and their isomers, cyclohexane, toluene, xylene, and mixtures thereof. Most preferable anti-solvents are diisopropyl ether and diethyl ether.

The solid obtained in step-(d) is collected by filtration or centrifugation.

The pure crystalline quetiapine besylate obtained by above process may be further dried in, for example, Vacuum Tray Dryer, Rotocon Vacuum Dryer, Vacuum Paddle Dryer or pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In another aspect of the present invention provides crystalline quetiapine besylate salt, with chemical purity greater than about 99%, specifically greater than about 99.5%, and more specifically greater than about 99.9% measured by HPLC.

The term "crude" in the specification refers to quetiapine having HPLC purity less than 98% and "pure" refers to having HPLC purity greater than 98%.

According to another aspect of the present invention, there is provided a stable and substantially pure amorphous form of quetiapine dibenzoyl-L-(+)-tartrate.

Amorphous form of quetiapine dibenzoyl-L-(+)-tartrate is characterized by its X-ray powder diffraction pattern, as shown in the accompanied drawing of FIG. 2. The X-ray powder diffraction pattern shows no peaks that are characteristic of amorphous form of quetiapine dibenzoyl-L-(+)-tartrate, thus demonstrating the amorphous nature of the product.

The term "substantially pure amorphous form of quetiapine dibenzoyl-L-(+)-tartrate" refers to the amorphous form of quetiapine dibenzoyl-L-(+)-tartrate having purity greater than about 98%, specifically greater than about 99%, more specifically greater than about 99.5% and still more specifically greater than about 99.9% (measured by HPLC).

In a preferred embodiment, the amorphous form of quetiapine dibenzoyl-L-(+)-tartrate obtained according the present invention having water content less than about 5% by weight, specifically less than about 1% by weight, and more specifically less than about 0.1% by weight, and still more specifically is essentially free from water.

According to another aspect of the present invention, a process is provided for preparation of a stable and substantially pure amorphous form of quetiapine dibenzoyl-L-(+)-tartrate, which comprises:
a) providing a solution of quetiapine free base in a suitable solvent;
b) adding dibenzoyl-L-(+)-tartaric acid to the solution obtained in step-(a);
c) optionally, heating the reaction mass obtained in step-(b) to form a clear solution; and
d) substantially removing the solvent from the solution to afford amorphous form of quetiapine dibenzoyl-L-(+)-tartrate.

The suitable solvent is selected from the group comprising water, alcohols, ketones, chlorinated hydrocarbons, nitriles, esters and the like, and mixtures thereof. Preferable solvents are ketones, alcohols, and mixtures thereof, more preferable solvents are ketones, and most preferably acetone.

Exemplary alcohol solvents include, but are not limited to, $C_1$ to $C_8$ straight or branched chain alcohol solvents such as methanol, ethanol, propanol, butanol, amyl alcohol, hexanol, and mixtures thereof. Specific alcohol solvents are methanol, ethanol, isopropyl alcohol, and mixtures, thereof, and most specific alcohol solvent is isopropyl alcohol. Exemplary ketone solvents include, but are not limited to, acetone, methyl ethyl ketone, methyl isobutyl ketone, methyl tert-butyl ketone and the like, and mixtures thereof. Exemplary nitrile solvents include, but are not limited to, acetonitrile and the like, and mixtures thereof. Exemplary ester solvents include, but are not limited to, ethyl acetate, isopropyl acetate, and the like and mixtures thereof. Exemplary chlorinated hydrocarbon solvents include, but are not limited to, methylene chloride, ethyl dichloride, chloroform and carbon tetrachloride or mixtures thereof. Specific chlorinated hydrocarbon solvent is methylene chloride.

Step-(a) of providing a solution of quetiapine free base includes dissolving quetiapine free base in the solvent, or obtaining an existing solution from a previous processing step.

Preferably the quetiapine free base is dissolved in the solvent at a temperature of above about 25° C., more preferably at about 25° C. to about 100° C., and still more preferably at about 25° C. to about 80° C.

The addition of dibenzoyl-L-(+)-tartaric acid in step-(b) is preferably carried out at a temperature of below about 50° C. for at least 10 minutes, and more preferably at a temperature of about 25° C. to about 50° C. from about 30 minutes to about 8 hours.

Usually, about 0.2 to 2.0 moles, specifically, about 0.2 to 1.2 moles of dibenzoyl-L-(+)-tartaric acid is used per 1 mole of quetiapine base.

The reaction mass in step-(c) is preferably heated at a temperature of about 40° C. to the reflux temperature of the solvent used for at least 20 minutes, and more preferably at the reflux temperature of the solvent used from about 30 minutes to about 4 hours.

Removal of solvent in step-(d) is accomplished by, for example, substantially complete evaporation of the solvent, concentrating the solution and filtering the solid under inert atmosphere. Alternatively, the solvent may also be removed by evaporation. Evaporation can be achieved at sub-zero temperatures by the lyophilisation or freeze-drying technique The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD"), or evaporated by spray drying to obtain a dry amorphous powder.

One of the preferred methodologies to remove the solvent involves spray-drying, in which a solution of quetiapine dibenzoyl-L-(+)-tartrate is sprayed into the spray drier at the flow rate ranging from 10 to 300 ml/hr, preferably flow rate is 40 to 200 ml/hr. The air inlet temperature to the spray drier used may range from 25 to 150° C., preferably from 60° C. to 110° C. and the outlet air temperature used may range from 30 to 90° C. Another preferred method is vertical agitated thin-film drying (or evaporation). Agitated thin film evaporation technology involves separating the volatile component using indirect heat transfer coupled with mechanical agitation of the flowing film under controlled condition.

The distillation process can be performed at atmospheric pressure or reduced pressure. Preferably the solvent is removed at a pressure of about 760 mm Hg or less, more preferably at about 400 mm Hg or less, still more preferably at about 80 mm Hg or less, and most preferably from about 30 to about 80 mm Hg.

The substantially pure amorphous form of quetiapine dibenzoyl-L-(+)-tartrate obtained by the above processes may be further dried in, for example, Vacuum Tray Dryer, Rotocon Vacuum Dryer, Vacuum Paddle Dryer or pilot plant Rota vapor, to further lower residual solvents.

According to another aspect of the present invention, there is provided a stable and substantially pure amorphous form of quetiapine di-p-toluoyl-L-(+)-tartrate.

Amorphous form of quetiapine di-p-toluoyl-L-(+)-tartrate is characterized by its X-ray powder diffraction pattern, as shown in the accompanied drawing of FIG. 3. The X-ray powder diffraction pattern shows no peaks that are characteristic of amorphous form of quetiapine di-p-toluoyl-L-(+)-tartrate, thus demonstrating the amorphous nature of the product.

The term "substantially pure amorphous form of quetiapine di-p-toluoyl-L-(+)-tartrate" refers to the amorphous form of quetiapine di-p-toluoyl-L-(+)-tartrate having purity greater than about 98%, specifically greater than about 99%, more specifically greater than about 99.5% and still more specifically greater than about 99.9% (measured by HPLC).

In a preferred embodiment, the amorphous form of quetiapine di-p-toluoyl-L-(+)-tartrate obtained according the present invention having water content less than about 5% by weight, specifically less than about 1% by weight, and more specifically less than about 0.1% by weight, and still more specifically is essentially free from water.

According to another aspect of the present invention, a process is provided for preparation of a stable and substantially pure amorphous form of quetiapine di-p-toluoyl-L-(+)-tartrate, which comprises:

a) providing a solution of quetiapine free base in a suitable solvent;
b) adding di-p-toluoyl-L-(+)-tartaric acid to the solution obtained in step-(a);
c) optionally, heating the reaction mass obtained in step-(b) to form a clear solution; and
d) substantially removing the solvent from the solution to afford amorphous form of quetiapine di-p-toluoyl-L-(+)-tartrate.

The suitable solvent is selected from the group comprising water, alcohols, ketones, chlorinated hydrocarbons, nitriles, esters and the like, and mixtures thereof. Preferable solvents are ketones, alcohols, and mixtures thereof, more preferable solvents are ketones, and most preferably acetone.

Exemplary alcohol solvents include, but are not limited to, $C_1$ to $C_8$ straight or branched chain alcohol solvents such as methanol, ethanol, propanol, butanol, amyl alcohol, hexanol, and mixtures thereof. Specific alcohol solvents are methanol, ethanol, isopropyl alcohol, and mixtures thereof, and most specific alcohol solvent is isopropyl alcohol. Exemplary ketone solvents include, but are not limited to, acetone, methyl ethyl ketone, methyl isobutyl ketone, methyl tert-butyl ketone and the like, and mixtures thereof. Exemplary nitrile solvents include, but are not limited to, acetonitrile and the like, and mixtures thereof. Exemplary ester solvents include, but are not limited to, ethyl acetate, isopropyl acetate, and the like and mixtures thereof. Exemplary chlorinated hydrocarbon solvents include, but are not limited to, methylene chloride, ethyl dichloride, chloroform and carbon tetrachloride or mixtures thereof. Specific chlorinated hydrocarbon solvent is methylene chloride.

Step-(a) of providing a solution of quetiapine free base includes dissolving quetiapine free base in the solvent, or obtaining an existing solution from a previous processing step.

Preferably the quetiapine free base is dissolved in the solvent at a temperature of above about 25° C., more preferably at about 25° C. to about 100° C., and still more preferably at about 25° C. to about 80° C.

The addition of di-p-toluoyl-L-(+)-tartaric acid in step-(b) is preferably carried out at a temperature of below about 50° C. for at least 10 minutes, and more preferably at a temperature of about 25° C. to about 50° C. from about 30 minutes to about 8 hours.

Usually, about 0.2 to 2.0 moles, specifically, about 0.2 to 1.2 moles of di-p-toluoyl-L-(+)-tartaric acid is used per 1 mole of quetiapine base.

The reaction mass in step-(c) is preferably heated at a temperature of about 40° C. to the reflux temperature of the solvent used for at least 20 minutes, and more preferably at the reflux temperature of the solvent used from about 30 minutes to about 4 hours.

Removal of solvent in step-(d) is accomplished by, for example, substantially complete evaporation of the solvent, concentrating the solution and filtering the solid under inert atmosphere. Alternatively, the solvent may also be removed by evaporation. Evaporation can be achieved at sub-zero temperatures by the lyophilisation or freeze-drying technique The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD"), or evaporated by spray drying to obtain a dry amorphous powder.

One of the preferred methodologies to remove the solvent involves spray-drying, in which a solution of quetiapine di-p-toluoyl-L-(+)-tartrate is sprayed into the spray drier at the flow rate ranging from 10 to 300 ml/hr, preferably flow rate is 40 to 200 ml/hr. The air inlet temperature to the spray drier used may range from 25 to 150° C., preferably from 60° C. to 110° C. and the outlet air temperature used may range from 30 to 90° C. Another preferred method is vertical agitated thin-film drying (or evaporation). Agitated thin film evaporation technology involves separating the volatile component using indirect heat transfer coupled with mechanical agitation of the flowing film under controlled condition.

The distillation process can be performed at atmospheric pressure or reduced pressure. Preferably the solvent is removed at a pressure of about 760 mm Hg or less, more preferably at about 400 mm Hg or less, still more preferably at about 80 mm Hg or less, and most preferably from about 30 to about 80 mm Hg.

The substantially pure amorphous form of quetiapine di-p-toluoyl-L-(+)-tartrate obtained by the above processes may be further dried in, for example, Vacuum Tray Dryer, Rotocon Vacuum Dryer, Vacuum Paddle Dryer or pilot plant Rota vapor, to further lower residual solvents.

According to another aspect of the present invention, there is provided a stable and substantially pure amorphous form of quetiapine nitrate.

Amorphous form of quetiapine nitrate is characterized by its X-ray powder diffraction pattern, as shown in the accompanied drawing of FIG. 4. The X-ray powder diffraction pattern shows no peaks that are characteristic of amorphous form of quetiapine nitrate, thus demonstrating the amorphous nature of the product.

The term "substantially pure amorphous form of quetiapine nitrate" refers to the amorphous form of quetiapine nitrate having purity greater than about 98%, specifically greater than about 99%, more specifically greater than about 99.5% and still more specifically greater than about 99.9% (measured by HPLC).

In a preferred embodiment, the amorphous form of quetiapine nitrate obtained according the present invention having water content less than about 5% by weight, specifically less than about 1% by weight, and more specifically less than about 0.1% by weight, and still more specifically is essentially free from water.

According to another aspect of the present invention, a process is provided for preparation of a stable and substantially pure amorphous form of quetiapine nitrate, which comprises:
a) providing a solution of quetiapine free base in a suitable solvent;
b) adding nitric acid to the solution obtained in step-(a);
c) optionally, stirring the reaction mass obtained in step-(b) to form a precipitate; and
d) collecting the precipitated amorphous form of quetiapine nitrate.

The suitable solvent is selected from the group comprising water, alcohols, ketones, and mixtures thereof. Preferable solvents are ketone solvents and most preferable solvent is acetone.

Exemplary alcohol solvents include, but are not limited to, $C_1$ to $C_8$ straight or branched chain alcohol solvents such as methanol, ethanol, propanol, butanol, amyl alcohol, hexanol, and mixtures thereof. Specific alcohol solvents are methanol, ethanol, isopropyl alcohol, and mixtures thereof, and most specific alcohol solvent is isopropyl alcohol. Exemplary ketone solvents include, but are not limited to, acetone, methyl ethyl ketone, methyl isobutyl ketone, methyl tert-butyl ketone and the like, and mixtures thereof.

Step-(a) of providing a solution of quetiapine free base includes dissolving quetiapine free base in the solvent, or obtaining an existing solution from a previous processing step.

Preferably the quetiapine free base is dissolved in the solvent at a temperature of above about 25° C., more preferably at about 25° C. to about 100° C., and still more preferably at about 25° C. to about 80° C.

The addition of nitric acid in step-(b) is preferably carried out at a temperature of below about 50° C. for at least 10 minutes, and more preferably at a temperature of about 15° C. to about 30° C. from about 30 minutes to about 1 hour.

Usually, about 0.2 to 2.0 moles, specifically, about 0.2 to 1.2 moles of nitric acid is used per 1 mole of quetiapine base.

The reaction mass in step-(c) is preferably stirred at a temperature of below about 50° C. for at least 20 minutes, and more preferably at a temperature of about 15° C. to about 30° C. from about 30 minutes to about 4 hours.

The precipitated solid obtained in step-(d) is collected by filtration or centrifugation.

The substantially pure amorphous form of quetiapine nitrate obtained by the above processes may be further dried in, for example, Vacuum Tray Dryer, Rotocon Vacuum Dryer, Vacuum Paddle Dryer or pilot plant Rota vapor, to further lower residual solvents.

According to another aspect of the present invention, there is provided a stable and substantially pure amorphous form of quetiapine citrate.

Amorphous form of quetiapine citrate is characterized by its X-ray powder diffraction pattern, as shown in the accompanied drawing of FIG. 5. The X-ray powder diffraction pattern shows no peaks that are characteristic of amorphous form of quetiapine citrate, thus demonstrating the amorphous nature of the product.

The term "substantially pure amorphous form of quetiapine citrate" refers to the amorphous form of quetiapine citrate having purity greater than about 98%, specifically greater than about 99%, more specifically greater than about 99.5% and still more specifically greater than about 99.9% (measured by HPLC).

In a preferred embodiment, the amorphous form of quetiapine citrate obtained according the present invention having water content less than about 5% by weight, specifically less than about 1% by weight, and more specifically less than about 0.1% by weight, and still more specifically is essentially free from water.

According to another aspect of the present invention, a process is provided for preparation of a stable and substantially pure amorphous form of quetiapine citrate, which comprises:
a) providing a solution of quetiapine free base in a suitable solvent;
b) adding citric acid to the solution obtained in step-(a);
c) optionally, heating the reaction mass obtained in step-(b) to form a clear solution; and
d) substantially removing the solvent from the solution to afford amorphous form of quetiapine citrate.

The suitable solvent is selected from the group comprising water, alcohols, ketones, chlorinated hydrocarbons, nitriles, esters and the like, and mixtures thereof. Preferable solvents are ketones, alcohols, and mixtures thereof, more preferable solvents are ketones, and most preferably acetone.

Step-(a) of providing a solution of quetiapine free base includes dissolving quetiapine free base in the solvent, or obtaining an existing solution from a previous processing step.

Preferably the quetiapine free base is dissolved in the solvent at a temperature of above about 25° C., more preferably at about 25° C. to about 100° C., and still more preferably at about 25° C. to about 80° C.

The addition of citric acid in step-(b) is preferably carried out at a temperature of below about 50° C. for at least 10 minutes, and more preferably at a temperature of about 25° C. to about 50° C. from about 30 minutes to about 2 hours.

Usually, about 0.2 to 2.0 moles, specifically, about 0.2 to 1.2 moles of citric is used per 1 mole of quetiapine base.

The reaction mass in step-(c) is preferably heated at a temperature of about 40° C. to the reflux temperature of the solvent used for at least 20 minutes, and more preferably at the reflux temperature of the solvent used from about 30 minutes to about 4 hours.

Removal of solvent in step-(d) is accomplished by, for example, substantially complete evaporation of the solvent, concentrating the solution and filtering the solid under inert atmosphere. Alternatively, the solvent may also be removed by evaporation. Evaporation can be achieved at sub-zero temperatures by the lyophilisation or freeze-drying technique The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD"), or evaporated by spray drying to obtain a dry amorphous powder.

One of the preferred methodologies to remove the solvent involves spray-drying, in which a solution of quetiapine citrate is sprayed into the spray drier at the flow rate ranging from 10 to 300 ml/hr, preferably flow rate is 40 to 200 ml/hr. The air inlet temperature to the spray drier used may range from 25 to 150° C., preferably from 60° C. to 110° C. and the outlet air temperature used may range from 30 to 90° C. Another preferred method is vertical agitated thin-film drying (or evaporation). Agitated thin film evaporation technology involves separating the volatile component using indirect heat transfer coupled with mechanical agitation of the flowing film under controlled condition.

The distillation process can be performed at atmospheric pressure or reduced pressure. Preferably the solvent is removed at a pressure of about 760 mm Hg or less, more preferably at about 400 mm Hg or less, still more preferably at about 80 mm Hg or less, and most preferably from about 30 to about 80 mm Hg.

The substantially pure amorphous form of quetiapine citrate obtained by the above processes may be further dried in, for example, Vacuum Tray Dryer, Rotocon Vacuum Dryer, Vacuum Paddle Dryer or pilot plant Rota vapor, to further lower residual solvents.

According to another aspect of the present invention, there is provided a crystalline quetiapine sulfate, designated as crystalline Form A, characterized by at least one of the following:

i) a powder X-ray diffraction pattern substantially in accordance with FIG. 6;
ii) a powder X-ray diffraction pattern having peaks at about 6.3, 8.1, 8.7, 9.7, 10.8, 12.4, 15.7, 17.8, 18.5, 19.4, 19.8, 20.1, 20.7, 21.2, 21.7, 22.9, 24.7, 25.0, 25.6, 25.9 and 26.2±0.2 degrees 2-theta substantially as depicted in FIG. 6; and
iii) a powder X-ray diffraction pattern having additional peaks at about 8.9, 12.1, 12.6, 13.9, 14.1, 16.5, 18.2, 18.8 and 22.2±0.2 degrees 2-theta substantially as depicted in FIG. 6.

The crystalline form A of quetiapine sulfate is stable, consistently reproducible and has good flow properties, and which is particularly suitable for bulk preparation and handling, and so, the novel quetiapine sulfate crystalline Form A is suitable for formulating quetiapine. Moreover, quetiapine sulfate crystalline Form A is useful intermediate in the preparation of quetiapine or a pharmaceutically acceptable salt thereof in high purity.

According to another aspect of the present invention, a process for the preparation of crystalline Form A of quetiapine sulfate is provided, which comprises:

a) providing a solution of quetiapine free base in a solvent selected from the group consisting of alcohols, ketones, and mixtures thereof;
b) adding sulfuric acid to the solution obtained in step-(a);
c) optionally, heating the reaction mass obtained in step-(b) to form a clear solution; and
d) isolating crystalline Form A of quetiapine sulfate from the solution.

The process can produce substantially pure crystalline Form A of quetiapine sulfate which can be isolated from the reaction mixture in conventional manner.

Exemplary alcohol solvents include, but are not limited to, $C_1$ to $C_8$ straight or branched chain alcohol solvents such as methanol, ethanol, isopropyl alcohol, butanol, amyl alcohol, hexanol, and mixtures thereof. Specific alcohol solvents are methanol, ethanol, isopropyl alcohol, and mixtures thereof, and most specifically isopropyl alcohol. Exemplary ketone solvents include, but are not limited to, acetone, methyl ethyl ketone, methyl isobutyl ketone, methyl tert-butyl ketone and the like, and mixtures thereof. Specific ketone solvent is acetone.

Step-(a) of providing a solution of quetiapine free base includes dissolving quetiapine free base in the solvent, or obtaining an existing solution from a previous processing step.

Preferably the quetiapine free base is dissolved in the solvent at a temperature of above about 25° C., more preferably at about 25° C. to about 100° C., and still more preferably at about 25° C. to about 80° C.

The addition of sulfuric acid in step-(b) is preferably carried out at a temperature of below about 50° C. for at least 10 minutes, and more preferably at a temperature of about 25° C. to about 50° C. from about 30 minutes to about 2 hours.

Usually, about 0.2 to 2.0 moles, specifically, about 0.2 to 1.2 moles of sulfuric acid is used per 1 mole of quetiapine base.

The reaction mass in step-(c) is preferably heated at a temperature of about 40° C. to about 80° C. for at least 20 minutes, and more preferably at a temperature of about 40° C. to about 75° C. from about 30 minutes to about 4 hours.

The isolation of pure quetiapine sulfate crystalline Form A in step-(d) may be carried out by forcible or spontaneous crystallization.

Spontaneous crystallization refers to crystallization without the help of an external aid such as seeding, cooling etc., and forcible crystallization refers to crystallization with the help of an external aid.

Forcible crystallization may be initiated by a method usually known in the art such as cooling, seeding, partial removal of the solvent from the solution, by adding an anti-solvent to the solution, or a combination thereof.

Preferably the crystallization is carried out by cooling the solution at a temperature of below 30° C., and more preferably at about 0° C. to about 25° C. The solid obtained in step-(d) is collected by filtration or centrifugation.

The pure quetiapine sulfate crystalline Form A obtained by above process may be further dried in, for example, Vacuum Tray Dryer, Rotocon Vacuum Dryer, Vacuum Paddle Dryer or pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In another aspect of the present invention provides quetiapine sulfate crystalline Form A with chemical purity greater than about 99%, specifically greater than about 99.5%, and more specifically greater than about 99.9% measured by HPLC.

According to another aspect of the present invention, there is provided a crystalline quetiapine hydrobromide, designated as crystalline Form B, characterized by at least one of the following:

i) a powder X-ray diffraction pattern substantially in accordance with FIG. 7; and
ii) a powder X-ray diffraction pattern having peaks at about 6.8, 12.9, 14.2, 23.5 and 24.2±0.2 degrees 2-theta substantially as depicted in FIG. 7.

The crystalline Form B of quetiapine hydrobromide is stable, consistently reproducible and has good flow properties, and which is particularly suitable for bulk preparation and handling, and so, the novel quetiapine hydrobromide crystalline Form B is suitable for formulating quetiapine.

According to another aspect of the present invention, a process for the preparation of crystalline Form B of quetiapine hydrobromide is provided, which comprises:

a) providing a solution of quetiapine free base in a ketonic solvent;
b) adding hydrobromic acid to the solution obtained in step-(a);
c) stirring the reaction mass obtained in step-(b) to form a clear solution;
d) concentrating the solution obtained step-(c) to form a residue;
e) adding a solvent mixture containing a ketonic solvent and an ether solvent to the residue;
f) heating the reaction mass obtained in step-(e); and
g) isolating crystalline Form B of quetiapine hydrobromide.

The process can produce quetiapine sulfate crystalline Form B in substantially pure form, which can be isolated from the reaction mixture in conventional manner.

Exemplary ketone solvents include, but are not limited to, acetone, methyl ethyl ketone, methyl isobutyl ketone, methyl tert-butyl ketone and the like, and mixtures thereof. Specific ketone solvent is acetone. Exemplary ether solvents include, but are not limited to, diisopropyl ether, diethyl ether, tetrahydrofuran, dioxane, and the like, and mixtures thereof. Most preferable solvents are acetone and diisopropyl ether.

Step-(a) of providing a solution of quetiapine free base includes dissolving quetiapine free base in the solvent, or obtaining an existing solution from a previous processing step.

Preferably the quetiapine free base is dissolved in the solvent at a temperature of above about 25° C., more preferably at about 25° C. to about 100° C., and still more preferably at about 25° C. to about 80° C.

The addition of hydrobromic acid in step-(b) is preferably carried out at a temperature of below about 50° C. for at least 10 minutes, and more preferably at a temperature of about 25° C. to about 50° C. from about 30 minutes to about 2 hours.

Usually, about 0.2 to 2.0 moles, specifically, about 0.2 to 1.2 moles of hydrobromic acid is used per 1 mole of quetiapine base.

The reaction mass in step-(c) is preferably stirred at a temperature of below about 50° C. for at least 20 minutes, and more preferably at a temperature of about 15° C. to about 30° C. from about 30 minutes to about 2 hours.

The addition of the solvent mixture in step-(e) is preferably carried out at a temperature of about 40° C. to about 80° C. for at least 20 minutes, and more preferably at a temperature of about 40° C. to about 75° C. from about 30 minutes to about 4 hours.

The reaction mass in step-(f) is preferably heated at a temperature of about 40° C. to the reflux temperature of the solvent used, and more preferably at the reflux temperature of the solvent used.

The isolation of pure crystalline Form B of quetiapine hydrobromide in step-(g) may be carried out by forcible or spontaneous crystallization.

Spontaneous crystallization refers to crystallization without the help of an external aid such as seeding, cooling etc., and forcible crystallization refers to crystallization with the help of an external aid.

Forcible crystallization may be initiated by a method usually known in the art such as cooling, seeding, partial removal of the solvent from the solution, by adding an anti-solvent to the solution, or a combination thereof.

Preferably the crystallization is carried out by cooling the solution at a temperature of below about 30° C., and more preferably at about 0° C. to about 25° C. The solid obtained in step-(d) is collected by filtration or centrifugation.

The pure quetiapine hydrobromide crystalline Form B obtained by above process may be further dried in, for example, Vacuum Tray Dryer, Rotocon Vacuum Dryer, Vacuum Paddle Dryer or pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In another aspect of the present invention provides quetiapine hydrobromide crystalline Form B with chemical purity greater than about 99%, specifically greater than about 99.5%, and more specifically greater than about 99.9% measured by HPLC.

Quetiapine free base used as starting material may be obtained by processes described in the prior art, for example by the process described in the U.S. Pat. No. 4,879,288.

In one embodiment, the substantially pure salt forms of quetiapine disclosed herein for use in the pharmaceutical compositions of the present invention, wherein 90 volume-percent of the particles ($D_{90}$) have a size of less than or equal to about 500 microns, specifically less than or equal to about 300 microns, more specifically less than or equal to about 200 microns, still more specifically less than or equal to about 100 microns, and most specifically less than or equal to about 15 microns.

In another embodiment, the particle sizes of substantially pure salt forms of quetiapine can be achieved via comminution, or a mechanical process of reducing the size of particles which includes any one or more of cutting, chipping, crushing, milling, grinding, micronizing, trituration or other particle size reduction methods known in the art, to bring the solid state forms the desired particle size range.

According to another aspect of the present invention, there is provided a method for treating or preventing psychosis associated with schizophrenia, comprising administering the salt forms of quetiapine, or a pharmaceutical composition that comprises salt forms of quetiapine, along with pharmaceutically acceptable excipients.

According to another aspect of the present invention, there is provided pharmaceutical compositions comprising the salt forms of quetiapine and one or more pharmaceutically acceptable excipients.

According to another aspect of the present invention, there is provided pharmaceutical compositions comprising the salt forms of quetiapine prepared according to processes of the present invention in any of its embodiments and one or more pharmaceutically acceptable excipients.

According to another aspect of the present invention, there is provided a process for preparing a pharmaceutical formulation comprising combining any one of the salt forms of quetiapine prepared according to processes of the present invention in any of its embodiments, with one or more pharmaceutically acceptable excipients.

Yet another embodiment of the present invention is directed to pharmaceutical compositions comprising at least a therapeutically effective amount of any one of the substantially pure salt forms of quetiapine of the present invention. Such pharmaceutical compositions may be administered to a mammalian patient in any dosage form, e.g., liquid, powder, elixir, injectable solution, etc. Dosage forms may be adapted for administration to the patient by oral, buccal, parenteral, ophthalmic, rectal and transdermal routes or any other acceptable route of administration. Oral dosage forms include, but are not limited to, tablets, pills, capsules, troches, sachets, suspensions, powders, lozenges, elixirs and the like. The salt forms of quetiapine of the present invention may also be administered as suppositories, ophthalmic ointments and suspensions, and parenteral suspensions, which are administered by other routes. The dosage forms may contain any one of the salt forms of quetiapine of the present invention as is or, alternatively, may contain any one of the salt forms of quetiapine of the present invention as part of a composition. The pharmaceutical compositions may further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrants described hereinabove.

In another embodiment of the present invention, there is provided pharmaceutical compositions comprising crystalline quetiapine besylate salt and one or more pharmaceutically acceptable excipients.

In another embodiment of the present invention, there is provided pharmaceutical compositions comprising amorphous quetiapine dibenzoyl-L-(+)-tartrate salt and one or more pharmaceutically acceptable excipients.

In another embodiment of the present invention, there is provided pharmaceutical compositions comprising amorphous quetiapine di-p-toluoyl-L-(+)-tartrate salt and one or more pharmaceutically acceptable excipients.

In another embodiment of the present invention, there is provided pharmaceutical compositions comprising amorphous quetiapine nitrate salt and one or more pharmaceutically acceptable excipients.

In another embodiment of the present invention, there is provided pharmaceutical compositions comprising amorphous quetiapine citrate salt and one or more pharmaceutically acceptable excipients.

In another embodiment of the present invention, there is provided pharmaceutical compositions comprising crystalline Form A of quetiapine sulfate salt and one or more pharmaceutically acceptable excipients.

In another embodiment of the present invention, there is provided pharmaceutical compositions comprising crystalline Form B of quetiapine hydrobromide salt and one or more pharmaceutically acceptable excipients.

Capsule dosages will contain the salt forms of quetiapine of the present invention within a capsule which may be coated with gelatin. Tablets and powders may also be coated with an enteric coating. The enteric-coated powder forms may have coatings containing at least phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, they may be employed with suitable plasticizers and/or extending agents. A coated capsule or tablet may have a coating on the surface thereof or may be a capsule or tablet comprising a powder or granules with an enteric-coating.

Tableting compositions may have few or many components depending upon the tableting method used, the release rate desired and other factors. For example, the compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols like mannitol and sorbitol, acrylate polymers and copolymers, as well as pectin, dextrin and gelatin.

Other excipients contemplated by the present invention include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

The following example is provided to enable one skilled in the art to practice the invention and is merely illustrate the process of this invention. However, it is not intended in any way to limit the scope of the present invention.

EXAMPLES

Example 1

Preparation of Quetiapine Sulfate Crystalline Form A

Quetiapine free base (5.0 g) was dissolved in isopropyl alcohol (50 ml) at room temperature. This was followed by addition of 98% sulfuric acid (1.28 g) at 30 to 35° C. The resulting gummy mass was heated to reflux and maintained for 15 minutes. The resulting mass was cooled at 25-30° C. and stirred for 1 hour. The precipitated product was collected by filtration, washed with isopropyl alcohol (25 ml) and dried to give the title compound as off white powder (5.88 g).

Example 2

Preparation of Quetiapine Hydrobromide Crystalline Form B

Quetiapine free base (5.0 g) was dissolved in acetone (50 ml) at room temperature. This was followed by addition of 48% aqueous hydrobromic acid (2 ml) at 30 to 35° C. The resulting solution was stirred for 1 hour at 20 to 25° C. Next, acetone was distilled under vacuum at 40 to 45° C. followed by addition of acetone (50 ml) and distilled under vacuum at 40 to 45° C. till complete removal. Next, acetone (50 ml) and diisopropyl ether (50 ml) were added at 40 to 45° C. The resulted mass was refluxed for 30 minutes and cooled at 20 to 25° C. and further stirred for 2.5 hours. The precipitated product was collected by filtration, washed with diisopropyl ether (25 ml) and dried to give the title compound as white powder (3.8 g).

Example 3

Preparation of Amorphous Quetiapine Nitrate

Quetiapine free base (5.0 g) was dissolved in acetone (50 ml) at room temperature. This was followed by the addition of 68 to 72% nitric acid (0.7 g) at 20 to 25° C. The resulting precipitated solid was stirred for 1 hour. The precipitated product was collected by filtration, washed with acetone (15 ml) and dried to give the title compound as white powder (4.0 g).

Example 4

Preparation of Crystalline Quetiapine Besylate

Quetiapine free base (5.0 g) was dissolved in acetone (50 ml) at room temperature. This was followed by the addition of benzene sulfonic acid (2.0 g) at 30 to 35° C. The resulting mass was heated at 40-45° C. and maintained for 30 minutes. The resulting mass was cooled at 25-30° C. This was followed by the addition of diethyl ether (50 ml) and stirred for 3 hours. The precipitated product was collected by filtration under nitrogen and washed with diethyl ether (25 ml) and dried under vacuum to give the title compound as off white powder (5.94 g).

Example 5

Preparation of Amorphous Quetiapine Citrate

Quetiapine free base (5.0 g) was dissolved in acetone (50 ml) at room temperature. This was followed by the addition of citric acid (1.1 g) at 30 to 35° C. The resulting mass was heated at reflux and maintained for 30 minutes. This was followed by the distillation of acetone and obtained solid was further dried under vacuum to give the title compound as off white powder (3.95 g).

Example 6

Preparation of Quetiapine Amorphous dibenzoyl-L-(+)-tartarate

Quetiapine free base (3.0 g) was dissolved in acetone (30 ml) at room temperature. This was followed by the addition of dibenzoyl-L-tartaric acid (1.4 g) at 30 to 35° C. The resulting mass was heated to reflux and maintained for 30 minutes. This was followed by the distillation of acetone and obtained solid was further dried under vacuum to give the title compound as off white powder (3.5 g).

Example 7

Preparation of Amorphous Quetiapine di-p-toluoyl-L-(+)-tartrate

Quetiapine free base (3.0 g) was dissolved in acetone (30 ml) at room temperature. To this solution was added di-p-toluoyl-L-tartaric acid (1.52 g) at 30 to 35° C. The resulting mass heated to reflux and maintained for 30 minutes. This was followed by the distillation of acetone and obtained solid was further dried under vacuum to give the title compound as off white powder (3.62 g).

We claim:

1. Solid state form of quetiapine sulfate salt characterized by one or more of the following properties:
   i) a powder X-ray diffraction pattern substantially in accordance with FIG. 6;
   ii) a powder X-ray diffraction pattern having peaks at about 6.3, 8.1, 8.7, 9.7, 10.8, 12.4, 15.7, 17.8, 18.5, 19.4, 19.8, 20.1, 20.7, 21.2, 21.7, 22.9, 24.7, 25.0, 25.6, 25.9 and 26.2±0.2 degrees 2-theta; and
   iii) a powder X-ray diffraction pattern having additional peaks at about 8.9, 12.1, 12.6, 13.9, 14.1, 16.5, 18.2, 18.8 and 22.2±0.2 degrees 2-theta.

2. A process for the preparation of solid state form of quetiapine sulfate salt of claim 1 comprising:
   a) providing a solution of quetiapine free base in a solvent selected from the group consisting of an alcohol, a ketone, and mixtures thereof;
   b) adding sulfuric acid to the solution obtained in step-(a);
   c) optionally, heating the reaction mass obtained in step-(b) to form a clear solution; and
   d) isolating crystalline Form A of quetiapine sulfate from the solution.

3. The process of claim 2, wherein the reaction mass in step (c) is heated at a temperature of about 40° C. to about 80° C. for at least 20 minutes.

4. The process of claim 2, wherein the isolation in step (d) is initiated by cooling, seeding, partial removal of the solvent from the solution, by adding an anti-solvent to the solution, or a combination thereof.

5. The process of claim 2, wherein the alcohol solvent used in step (a) is selected from the group consisting of methanol, ethanol, isopropyl alcohol, butanol, amyl alcohol, hexanol, and mixtures thereof; and wherein the ketone solvent used in step (a) is selected from the group consisting of acetone, methyl ethyl ketone, methyl isobutyl ketone, methyl tert-butyl ketone, and mixtures thereof.

6. The process of claim 5, wherein the alcohol solvent is isopropyl alcohol and the ketone is acetone.

7. The process of claim 4, wherein the isolation is carried out by cooling the solution at a temperature of below 30° C.

8. A pharmaceutical composition comprising the solid state forms of quetiapine sulfate salt of claim 1 and one or more pharmaceutically acceptable excipients.

* * * * *